(12) United States Patent
Weiss

(10) Patent No.: US 9,725,493 B2
(45) Date of Patent: Aug. 8, 2017

(54) N-TERMINAL TRUNCATED INSULIN ANALOGUES

(71) Applicant: CASE WESTERN RESERVE UNIVERSITY, Cleveland, OH (US)

(72) Inventor: Michael A. Weiss, Moreland Hills, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 14/762,712

(22) PCT Filed: Jan. 22, 2014

(86) PCT No.: PCT/US2014/012615
§ 371 (c)(1),
(2) Date: Jul. 22, 2015

(87) PCT Pub. No.: WO2014/116753
PCT Pub. Date: Jul. 31, 2014

(65) Prior Publication Data
US 2015/0353621 A1    Dec. 10, 2015

Related U.S. Application Data

(60) Provisional application No. 61/755,020, filed on Jan. 22, 2013.

(51) Int. Cl.
| A61K 38/28 | (2006.01) |
| C07K 14/62 | (2006.01) |
| C12P 21/06 | (2006.01) |
| A61K 38/00 | (2006.01) |

(52) U.S. Cl.
CPC ............. *C07K 14/62* (2013.01); *A61K 38/28* (2013.01); *C12P 21/06* (2013.01); *A61K 38/00* (2013.01)

(58) Field of Classification Search
CPC ............................... A61K 38/28; C07K 14/62
See application file for complete search history.

(56) References Cited

FOREIGN PATENT DOCUMENTS

| EP | 0925792 | * | 6/1999 |
| WO | WO 00/64494 | * | 11/2000 |

OTHER PUBLICATIONS

Schwartz, Gerald and Katsoyannis, Panayotis G., "Synthesis of Des(tetrapeptide B1-4) and Des(pentapeptide B1-5) Human Insulins. Two Biologically Active Analogues", American Chemical Society, 1978, pp.
EP14742940 Search Report dated Feb. 15, 2017.

* cited by examiner

Primary Examiner — Gyan Chandra
(74) Attorney, Agent, or Firm — Hahn Loeser & Parks LLP

(57) ABSTRACT

An insulin analogue contains a foreshortened B-chain polypeptide lacking residues B1-B3 and optionally contains an additional substitution in the C-terminal B23-B30 segment of the B-chain. The insulin analogue lacking residues B1-B3 may contain substitutions at B28 and/or B29 that confer rapid action and optionally a non-standard substitution at B24. The analogue may be an analogue of a mammalian insulin, such as human insulin. A nucleic acid encoding such an insulin analogue is also provided. A method of treating a patient comprises administering a physiologically effective amount of the insulin analogue or a physiologically acceptable salt thereof to a patient. A method of semi-synthesis is provided using an unprotected octapeptide by means of modification of an endogenous tryptic site by non-standard amino-acid substitutions.

10 Claims, 7 Drawing Sheets

PROINSULIN

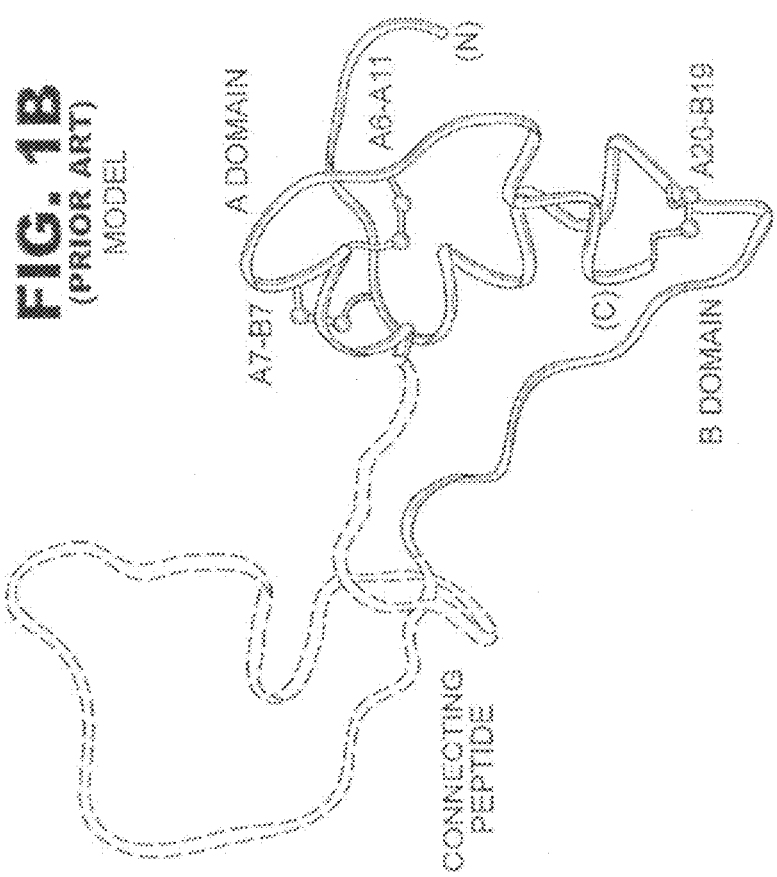

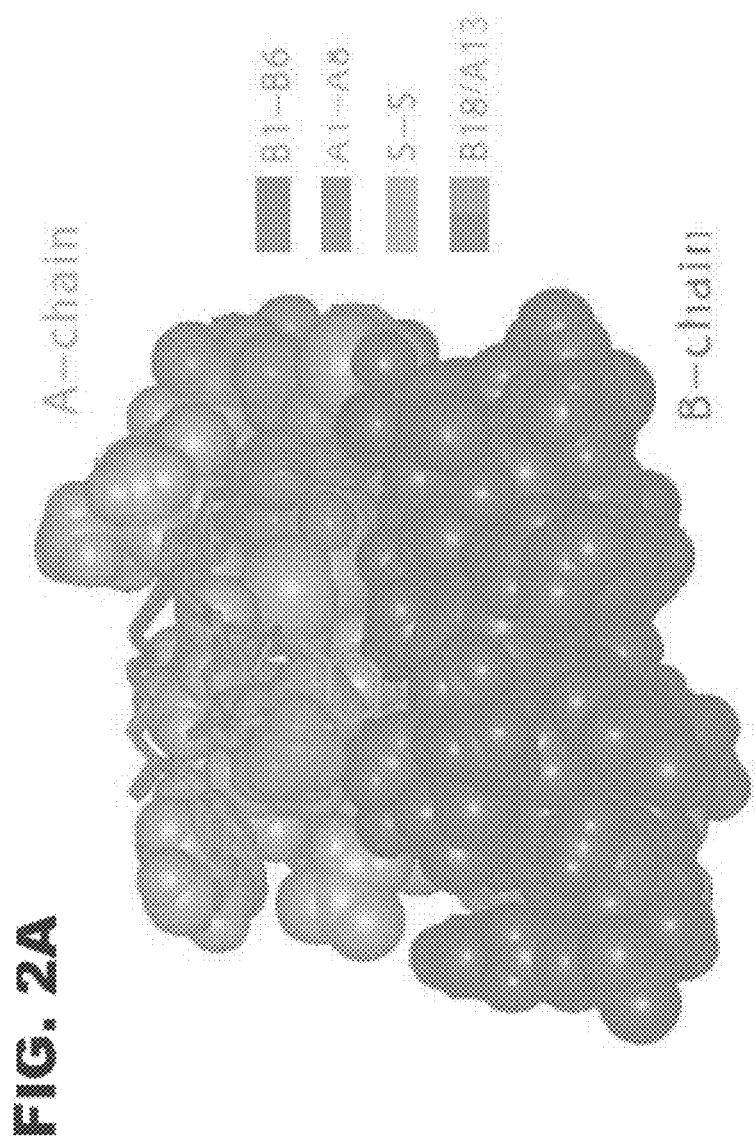

SEQUENCE LISTING

<160> NUMBER OF SEQ ID NOS: 20

<210> SEQ ID NO 1
<211> LENGTH: 86
<212> TYPE: PRT
<213> ORGANISM: Homo sapiens

<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 2
<211> LENGTH: 21
<212> TYPE: PRT
<213> ORGANISM: Homo sapiens

<400> SEQUENCE: 2

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 3
<211> LENGTH: 30
<212> TYPE: PRT
<213> ORGANISM: Homo sapiens

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 4
<211> LENGTH: 30
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is Arg or Lys
<220> FEATURE:
<221> NAME/KEY: MISC_FEATURE
<222> LOCATION: (29)..(29)
<223> OTHER INFORMATION: Xaa is Glu or Lys

<400> SEQUENCE: 4

Phe Val Xaa Gln His Leu Cys Gly Ser His Leu Val Glu Ala Leu Tyr
1               5                   10                  15

Leu Val Cys Gly Glu Arg Gly Phe Phe Tyr Thr Pro Xaa Thr
            20                  25                  30

<210> SEQ ID NO 5
<211> LENGTH: 27
<212> TYPE: PRT
<213> ORGANISM: Homo sapiens
<220> FEATURE:
<221> NAME/KEY: MISC_FEATURE
<222> LOCATION: (7)..(7)

```
<223> OTHER INFORMATION: Xaa is His, Asp, Pro, or Glu
<220> FEATURE:
<221> NAME/KEY: MISC_FEATURE
<222> LOCATION: (21)..(21)
<223> OTHER INFORMATION: Xaa is Phe, Cyclohexanylalanine,
      penta-fluoro-Phe, 2F-Phe, 2-Cl-Phe, 2-Br-Phe, 4F-Phe, 4-Cl-Phe,
      or 4-Br-Phe
<220> FEATURE:
<221> NAME/KEY: MISC_FEATURE
<222> LOCATION: (26)..(26)
<223> OTHER INFORMATION: Xaa is Glu, Lys, Ornithine, Diaminobutyric
      acid, Diaminoproprionic acid, Norleucine, Aminobutric acid, or
      Aminoproprionic acid

<400> SEQUENCE: 5

Gln His Leu Cys Gly Ser Xaa Leu Val Glu Ala Leu Tyr Leu Val Cys
1               5                   10                  15

Gly Glu Arg Gly Xaa Phe Tyr Thr Pro Xaa Thr
            20                  25

<210> SEQ ID NO 6
<211> LENGTH: 27
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa is His, Asp, Pro, or Glu
<220> FEATURE:
<221> NAME/KEY: MISC_FEATURE
<222> LOCATION: (21)..(21)
<223> OTHER INFORMATION: Xaa is Phe, Cyclohexanylalanine,
      penta-fluoro-Phe, 2F-Phe, 2-Cl-Phe, 2-Br-Phe, 4F-Phe, 4-Cl-Phe, or
      4-Br-Phe
<220> FEATURE:
<221> NAME/KEY: MISC_FEATURE
<222> LOCATION: (25)..(25)
<223> OTHER INFORMATION: Xaa is Lys, Arg, Ala, Glu, Gln, or Val

<400> SEQUENCE: 6

Gln His Leu Cys Gly Ser Xaa Leu Val Glu Ala Leu Tyr Leu Val Cys
1               5                   10                  15

Gly Glu Arg Gly Xaa Phe Tyr Thr Xaa Pro Thr
            20                  25

<210> SEQ ID NO 7
<211> LENGTH: 27
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa is His, Asp, Pro, or Glu
<220> FEATURE:
<221> NAME/KEY: MISC_FEATURE
<222> LOCATION: (21)..(21)
<223> OTHER INFORMATION: Xaa is Phe, Cyclohexanylalanine,
      penta-fluoro-Phe, 2F-Phe, 2-Cl-Phe, 2-Br-Phe, 4F-Phe, 4-Cl-Phe, or
      4-Br-Phe

<400> SEQUENCE: 7

Gln His Leu Cys Gly Ser Xaa Leu Val Glu Ala Leu Tyr Leu Val Cys
1               5                   10                  15

Gly Glu Arg Gly Xaa Phe Tyr Thr Pro Glu Thr
            20                  25

<210> SEQ ID NO 8
<211> LENGTH: 21
<212> TYPE: PRT
<213> ORGANISM: Homo sapiens
```

```
<220> FEATURE:
<221> NAME/KEY: MISC_FEATURE
<222> LOCATION: (8)..(8)
<223> OTHER INFORMATION: Xaa is Arg, Gln, Glu, His, Lys, or Thr

<400> SEQUENCE: 8

Gly Ile Val Glu Gln Cys Cys Xaa Ser Ile Cys Ser Leu Tyr Gln Leu
1               5                   10                  15

Glu Asn Tyr Cys Asn
            20

<210> SEQ ID NO 9
<211> LENGTH: 52
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is Arg or Lys
<220> FEATURE:
<221> NAME/KEY: MISC_FEATURE
<222> LOCATION: (24)..(24)
<223> OTHER INFORMATION: Xaa is Phe, Cyclohexanylalanine,
      penta-fluoro-Phe, 2F-Phe, 2-Cl-Phe, 2-Br-Phe, 4F-Phe, 4-Cl-Phe, or
      4-Br-Phe
<220> FEATURE:
<221> NAME/KEY: MISC_FEATURE
<222> LOCATION: (28)..(28)
<223> OTHER INFORMATION: Xaa is Pro, Lys, or Asp
<220> FEATURE:
<221> NAME/KEY: MISC_FEATURE
<222> LOCATION: (29)..(29)
<223> OTHER INFORMATION: Xaa is Glu, Lys or Pro
<220> FEATURE:
<221> NAME/KEY: MISC_FEATURE
<222> LOCATION: (31)..(31)
<223> OTHER INFORMATION: Xaa is 0-34 of any amino acid or a break in the
      amino-acid chain
<220> FEATURE:
<221> NAME/KEY: MISC_FEATURE
<222> LOCATION: (35)..(35)
<223> OTHER INFORMATION: Xaa is Glu, Arg or Lys
<220> FEATURE:
<221> NAME/KEY: MISC_FEATURE
<222> LOCATION: (39)..(39)
<223> OTHER INFORMATION: Xaa is His, Lys, Arg, Glu, Gln or Thr

<400> SEQUENCE: 9

Phe Val Xaa Gln His Leu Cys Gly Ser His Leu Val Glu Ala Leu Tyr
1               5                   10                  15

Leu Val Cys Gly Glu Arg Gly Xaa Phe Tyr Thr Xaa Xaa Thr Xaa Gly
            20                  25                  30

Ile Val Xaa Gln Cys Cys Xaa Ser Ile Cys Ser Leu Tyr Gln Leu Glu
        35                  40                  45

Asn Tyr Cys Asn
    50

<210> SEQ ID NO 10
<211> LENGTH: 8
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa is Ornithine

<400> SEQUENCE: 10

Gly Phe Phe Tyr Thr Pro Xaa Thr
1               5
```

<210> SEQ ID NO 11
<211> LENGTH: 8
<212> TYPE: PRT
<213> ORGANISM: Homo sapiens

<400> SEQUENCE: 11

Gly Phe Phe Tyr Thr Pro Glu Thr
1               5

<210> SEQ ID NO 12
<211> LENGTH: 8
<212> TYPE: PRT
<213> ORGANISM: Homo sapiens

<400> SEQUENCE: 12

Gly Phe Phe Tyr Thr Lys Pro Thr
1               5

<210> SEQ ID NO 13
<211> LENGTH: 8
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Cyclohexanylalanine, penta-fluoro-Phe,
      2F-Phe, 2-Cl-Phe, 2-Br-Phe, 4F-Phe, 4-Cl-Phe, or 4-Br-Phe

<400> SEQUENCE: 13

Gly Xaa Phe Tyr Thr Lys Pro Thr
1               5

<210> SEQ ID NO 14
<211> LENGTH: 8
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Cyclohexanylalanine, penta-fluoro-Phe,
      2F-Phe, 2-Cl-Phe, 2-Br-Phe, 4F-Phe, 4-Cl-Phe, or 4-Br-Phe
<220> FEATURE:
<221> NAME/KEY: MISC_FEATURE
<222> LOCATION: (7)..(7)
<223> OTHER INFORMATION: Xaa is Ornithine

<400> SEQUENCE: 14

Gly Xaa Phe Tyr Thr Pro Xaa Thr
1               5

<210> SEQ ID NO 15
<211> LENGTH: 8
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Cyclohexanylalanine, penta-fluoro-Phe,
      2F-Phe, 2-Cl-Phe, 2-Br-Phe, 4F-Phe, 4-Cl-Phe, or 4-Br-Phe

<400> SEQUENCE: 15

Gly Xaa Phe Tyr Thr Pro Glu Thr
1               5

<210> SEQ ID NO 16
<211> LENGTH: 8
<212> TYPE: PRT
<213> ORGANISM: Homo sapiens

```
<220> FEATURE:
<221> NAME/KEY: MISC_FEATURE
<222> LOCATION: (2)..(2)
<223> OTHER INFORMATION: Xaa is Cyclohexanylalanine, penta-fluoro-Phe,
      2F-Phe, 2-Cl-Phe, 2-Br-Phe, 4F-Phe, 4-Cl-Phe, or 4-Br-Phe
<220> FEATURE:
<221> NAME/KEY: MISC_FEATURE
<222> LOCATION: (7)..(7)
<223> OTHER INFORMATION: Xaa is Glu, Lys, Ornithine, Diaminobutyric
      acid, Diaminoproprionic acid, Norleucine, Aminobutric acid, or
      Aminoproprionic acid

<400> SEQUENCE: 16

Gly Xaa Phe Tyr Thr Asp Xaa Thr
1               5

<210> SEQ ID NO 17
<211> LENGTH: 90
<212> TYPE: DNA
<213> ORGANISM: Homo sapiens
<220> FEATURE:
<221> NAME/KEY: misc_feature
<222> LOCATION: (6)..(8)
<223> OTHER INFORMATION: NNN is AGG, AGA, CGG, CGC, AAG or AAA
<220> FEATURE:
<221> NAME/KEY: misc_feature
<222> LOCATION: (9)..(9)
<223> OTHER INFORMATION: n is a, c, g, or t

<400> SEQUENCE: 17
tttgtgnnnc aacacctgtg cggctcacac ctggtggaag ctctctacct agtgtgcggg      60
gaacgaggct agttctacac acccaagacc                                      90

<210> SEQ ID NO 18
<211> LENGTH: 90
<212> TYPE: DNA
<213> ORGANISM: Homo sapiens
<220> FEATURE:
<221> NAME/KEY: misc_feature
<222> LOCATION: (7)..(9)
<223> OTHER INFORMATION: NNN is AGA, CGU, AGG, AAG or AAA

<400> SEQUENCE: 18
tttgttnnnc aacatttgtg tggttctcat ttggttgaag ctttgtactt ggtttgtggt      60
gaaagaggtt agttttacac tccaaagact                                      90

<210> SEQ ID NO 19
<211> LENGTH: 261
<212> TYPE: DNA
<213> ORGANISM: Homo sapiens
<220> FEATURE:
<221> NAME/KEY: misc_feature
<222> LOCATION: (6)..(8)
<223> OTHER INFORMATION: NNN is AGG, AGA, CGG, CGC, AAG or AAA

<400> SEQUENCE: 19
tttgtnnncc aacacctgtg cggctcacac ctggtggaag ctctctacct agtgtgcggg      60
gaacgaggct agttctacac acccaagacc cgccggagg cagaggacct gcaggtgggg     120
caggtggagc tgggcggcgg ccctggtgca ggcagcctgc agcccttggc cctggagggg     180
tccctgcaga agcgtggcat tgtgaacaa tgctgtacca gcatctgctc cctctaccag     240
ctggagaact actgcaacta g                                              261

<210> SEQ ID NO 20
<211> LENGTH: 260
<212> TYPE: DNA
```

```
<213> ORGANISM: Homo sapiens
<220> FEATURE:
<221> NAME/KEY: misc_feature
<222> LOCATION: (7)..(9)
<223> OTHER INFORMATION: NNN is AGA, CGU, AGG, AAG or AAA

<400> SEQUENCE: 20
tttgttnnnc aacatttgtg tggttctcat ttggttgaag ctttgtactt ggtttgtgtg      60
aaagaggtta gttttacact ccaaagacta gaagagaagc tgaagatttg caagttggtc     120
aagttgaatt gggtggtggt ccaggtgctg gttctttgca accattggct ttggaaggtt     180
ctttgcaaaa gagaggtatt gttgaacaat gttgtacttc tatttgttct ttgtaccaat     240
tggaaaacta ctgtaactaa                                                 260
```

N-TERMINAL TRUNCATED INSULIN ANALOGUES

CROSS-REFERENCE TO RELATED APPLICATION

This application claims priority to and the benefit of PCT/US2014/012615 filed Jan. 22, 2014, which claims the benefit of U.S. Provisional Application Ser. No. 61/755,020 filed Jan. 22, 2013, the contents of which are hereby incorporated by reference in their entirety.

STATEMENT REGARDING FEDERALLY SPONSORED RESEARCH OR DEVELOPMENT

This invention was made with government support awarded by the National Institutes of Health under grant numbers DK040949 and DK074176. The U.S. government has certain rights to the invention.

BACKGROUND OF THE INVENTION

This invention relates to polypeptide hormone analogues that exhibits enhanced pharmaceutical properties, such as more rapid pharmacokinetics and/or augmented resistance to thermal fibrillation above room temperature. More particularly, this invention relates to insulin analogues that are modified by deletion of residues B1-B3 in combination with other modifications of the A-chain or B-chain. Such non-standard sequences may optionally contain standard amino-acid substitutions at other sites in the A or B chains of an insulin analogue.

The engineering of truncated and/or non-standard proteins, including therapeutic agents and vaccines, may have broad medical and societal benefits. An example of a medical benefit would be optimization of the pharmacokinetic properties of a protein. An example of a further societal benefit would be the engineering of proteins more refractory than standard proteins with respect to degradation at or above room temperature for use in regions of the developing world where electricity and refrigeration are not consistently available. An example of a therapeutic protein is provided by insulin. Analogues of insulin containing non-standard amino-acid substitutions may in principle exhibit superior properties with respect to pharmacokinetics or resistance to thermal degradation. The challenge posed by the pharmacokinetics of insulin absorption following subcutaneous injection affects the ability of patients to achieve tight glycemic control and constrains the safety and performance of insulin pumps. The challenge posed by its physical degradation is deepened by the pending epidemic of diabetes mellitus in Africa and Asia. These issues are often coupled as modifications known in the art to accelerate absorption following subcutaneous injection usually worsen the resistance of insulin to chemical and/or physical degradation. Because fibrillation poses the major route of degradation above room temperature, the design of fibrillation-resistant formulations may enhance the safety and efficacy of insulin replacement therapy in such challenged regions. The present invention pertains to the use of a truncated B-chain lacking residues B1-B3 in combination with standard or non-standard substitutions elsewhere in the A-chain or B-chain to modify and improve distinct properties of insulin. During the past decade specific chemical modifications to the insulin molecule have been described that selectively modify one or another particular property of the protein to facilitate an application of interest. Whereas at the beginning of the recombinant DNA era (1980) wild-type human insulin was envisaged as being optimal for use in diverse therapeutic contexts, the broad clinical use of insulin analogues in the past decade suggests that a suite of analogs, each tailored to address a specific unmet need, would provide significant medical and societal benefits.

Administration of insulin has long been established as a treatment for diabetes mellitus. Insulin is a small globular protein that plays a central role in metabolism in vertebrates. Insulin contains two chains, an A chain, containing 21 residues, and a B chain containing 30 residues. The hormone is stored in the pancreatic β-cell as a $Zn^{2+}$-stabilized hexamer, but functions as a $Zn^{2+}$-free monomer in the bloodstream. Insulin is the product of a single-chain precursor, proinsulin, in which a connecting region (35 residues) links the C-terminal residue of B chain (residue B30) to the N-terminal residue of the A chain (FIG. 1A). A variety of evidence indicates that it consists of an insulin-like core and disordered connecting peptide (FIG. 1B). Formation of three specific disulfide bridges (A6-A11, A7-B7, and A20-B19; FIGS. 1A and 1B) is thought to be coupled to oxidative folding of proinsulin in the rough endoplasmic reticulum (ER). Proinsulin assembles to form soluble $Zn^{2+}$-coordinated hexamers shortly after export from ER to the Golgi apparatus. Endoproteolytic digestion and conversion to insulin occurs in immature secretory granules followed by morphological condensation. Crystalline arrays of zinc insulin hexamers within mature storage granules have been visualized by electron microscopy (EM). The sequence of insulin is shown in schematic form in FIG. 1C. Individual residues are indicated by the identity of the amino acid (typically using a standard three-letter code), the chain and sequence position (typically as a superscript).

The pharmacokinetic features of insulin absorption after subcutaneous injection have been found to correlate with the rate of disassembly of the insulin hexamer. Although not wishing the present invention to be constrained by theory, modifications to the insulin molecule that lead to accelerated disassembly of the insulin hexamer are thought to promote more rapid absorption of insulin monomers and dimers from the subcutaneous depot into the bloodstream. A major goal of insulin replacement therapy in patients with diabetes mellitus is tight control of the blood glucose concentration to prevent its excursion above or below the normal range characteristic of healthy human subjects. Excursions below the normal range are associated with immediate adrenergic or neuroglycopenic symptoms, which in severe episodes lead to convulsions, coma, and death. Excursions above the normal range are associated with increased long-term risk of microvascular disease, including retinopathy, blindness, and renal failure. Because the pharmacokinetics of absorption of wild-type human insulin following subcutaneous injection is often too slow and too prolonged relative to the physiological requirements of post-prandial metabolic homeostasis, considerable efforts have been expended during the past 20 years to develop insulin analogues that exhibit more rapid absorption with pharmacodynamic effects that are more rapid in onset and less prolonged in duration. Examples of such rapid-acting analogues known in the art are $[Lys^{B28}, Pro^{B29}]$-insulin (KP-insulin, the active component of Humalog®), [AspB28]-insulin (Novalog®), and $[Lys^{B3}, Glu^{B29}]$-insulin (Apidra®). Although widely used in clinical practice, these analogues exhibit two principal limitations. First, although their pharmacokinetic and pharmacodynamic profiles are more rapid than those of wild-type insulin, they are not rapid enough in many patients to optimize glycemic control or enable the safe and effective use of algorithmbased insulin pumps (closed-loop systems). Second, the amino-acid substitutions in these analogues impair the thermodynamic stability of insulin and exacerbate its susceptibility to fibrillation above room temperature. Thus, the safety, efficacy, and real-world convenience of these products have been limited by a trade-off between accelerated absorption and accelerated degradation.

Fibrillation, which is a serious concern in the manufacture, storage and use of insulin and insulin analogues for the treatment of diabetes mellitus, is enhanced with higher temperature, lower pH, agitation, or the presence of urea, guanidine, ethanol co-solvent, or hydrophobic surfaces. Current US drug regulations demand that insulin be discarded if fibrillation occurs at a level of one percent or more. Because fibrillation is enhanced at higher temperatures, patients with diabetes mellitus optimally must keep insulin refrigerated prior to use. Fibrillation of insulin or an insulin analogue can be a particular concern for such patients utilizing an external insulin pump, in which small amounts of insulin or insulin analogue are injected into the patient's body at regular intervals. In such a usage, the insulin or insulin analogue is not kept refrigerated within the pump apparatus, and fibrillation of insulin can result in blockage of the catheter used to inject insulin or insulin analogue into the body, potentially resulting in unpredictable fluctuations in blood glucose levels or even dangerous hyperglycemia. At least one recent report has indicated that insulin Lispro (KP-insulin, an analogue in which residues B28 and B29 are interchanged relative to their positions in wild-type human insulin; trade name Humalog®) may be particularly susceptible to fibrillation and resulting obstruction of insulin pump catheters. Insulin exhibits an increase in degradation rate of 10-fold or more for each 10° C. increment in temperature above 25° C.; accordingly, guidelines call for storage at temperatures <30° C. and preferably with refrigeration.

The present theory of protein fibrillation posits that the mechanism of fibrillation proceeds via a partially folded intermediate state, which in turn aggregates to form an amyloidogenic nucleus. In this theory, it is possible that amino-acid substitutions that stabilize the native state may or may not stabilize the partially folded intermediate state and may or may not increase (or decrease) the free-energy barrier between the native state and the intermediate state. Therefore, the current theory indicates that the tendency of a given amino-acid substitution in the insulin molecule to increase or decrease the risk of fibrillation is highly unpredictable.

Initial steps in the formation of an amyloidogenic nucleus may involve non-native hydrophobic interactions between nonpolar side chains that are either exposed on the surface of native insulin or are transiently exposed due to partial protein unfolding. Residues B1, B2, and B3 (Phe$^{B1}$-Val$^{B2}$-Asn$^{B3}$) exhibit significant exposure in crystal structures of wild-type insulin and substantial variability in their positioning (FIG. 2A). Residues B1-B3 are also less well ordered in NMR studies of engineered insulin monomers in solution as indicated by $^1$H-NMR resonance line widths, $^{13}$C-NMR chemical shifts, and paucity of long-range inter-residue nuclear Overhauser effects (NOEs) (FIG. 2B). Despite the conservation of these residues among mammalian insulin sequences, studies of synthetic analogs has shown that residues B1-B5 may be deleted from the B-chain without significant loss of binding to the insulin receptor and without significant loss of biological activity. Studies of the folding and secretion of wild-type and mutant proinsulins have nonetheless shown that residues B1-B5, singly and in combination, contribute to the efficiency and fidelity of disulfide pairing in the endoplasmic reticulum (Liu, M., Hua, Q. X., Hu, S. Q., Jia, W., Yang, Y., Saith, S. E., Whittaker, J., Aryan, P. & Weiss, M. A. (2010)). Deciphering the hidden informational content of protein sequences: foldability of proinsulin hinges on a flexible arm that is dispensable in the mature hormone. *J. Biol. Chem.* 285, 30989-31001). In particular, diverse polar or charged amino-acid substitutions at position B1 have been found to impair the cellular folding and secretion of proinsulin in a human cell line in culture. Residue Phe$^{B1}$ may therefore be regarded as a "hydrophobic anchor" in the folding process. The B1-B5 arm of the B-chain represents a key folding element within the pancreatic beta-cell.

There is a need, therefore for an insulin analogue that displays increased resistance to fibrillation above room temperature while retaining rapid hexamer disassembly and while exhibiting at least a portion of the activity of the corresponding wild-type insulin and maintaining at least a portion of its chemical and/or physical stability.

SUMMARY OF THE INVENTION

It is, therefore, an aspect of the present invention to provide insulin analogues that provide augmented resistance to fibrillation above room temperature while retaining rapid hexamer disassembly and hence accelerated absorption following subcutaneous injection. The present invention addresses previous limitations for fast-acting insulin analogues, namely, that they are more susceptible to fibrillation than wild-type insulin. The claimed invention exploits the dispensability of residues B1-B3 once disulfide pairing and protein folding have been achieved in the manufacturing process. Removal of residues B1-B3 is accomplished through the action of trypsin on a precursor that contains Lys or Arg at position B3 in the place of the wild-type residue Asn$^{B3}$. An example of such a precursor is the analog insulin glulisine, the active component of the product Apidra (Sanofi-Aventis). Analogs lacking residues Phe$^{B1}$-Val$^{B2}$-Asn$^{B3}$ thus contain a foreshortened B-chain (27 residues). The foreshortened B-chain confers resistance to fibrillation above room temperature while enabling native-like binding to the insulin receptor.

The essence of this invention is that foreshortening of the B-chain by N-terminal removal of residues B1-B3 protects the protein from fibrillation above room temperature and may be accomplished following the efficient folding and disulfide pairing of a precursor polypeptide containing residues Phe$^{B1}$, Val$^{B2}$, and either Lys or Arg at position B3 to introduce a new tryptic site. The tryptic product des-[B1-B3]-des-B23-B30]-insulin analogue provides in turn a precursor for the trypsin-mediated semi-synthesis of insulin analogs containing one or more substitutions or non-standard modifications in the C-terminal B23-B30 segment; critically, trypsin-mediated semi-synthesis "repairs" the C-terminal deletion of residues B23-B30 but does not restore the B1-B3 segment. This order of steps (i.e., folding prior to tryptic digestion) circumvents the folding defect otherwise introduced by removal of residues B1-B3 prior to disulfide pairing. The starting material may be a mature insulin analogue containing Lys or Arg at position B3, an insulin analogue containing Lys or Arg at position B3 and an additional substitution at A8, a proinsulin analogue containing Lys or Arg at position B3, proinsulin analogue containing Lys or Arg at position B3 and an additional substitution at A8, or corresponding single-chain biosynthetic precursor containing Lys or Arg at position B3 and whose post-folding tryptic digestion yields a des-[B1-B3]-des-B23-B30]-insulin analogue amenable to semi-synthesis to provide a des-[B1-B3]-insulin analogue.

In general, the present invention provides an insulin analogue comprising a foreshortened B-chain polypeptide that lacks residues B1-B3 in combination with one or more additional substitutions in the A- or B-chain. Unless stated otherwise, the locations of amino acids should be understood to be the location in comparison to wild type insulin. Therefore in a des-[B1-B3] insulin analogue, the seventh amino acid in the B chain would still be denoted as being at position B10, for example. In one example, the foreshortened B-chain polypeptide incorporates an Ornithine (Orn), Norleucine (Nle), or Glutamic acid (Glu) at position B29. In another embodiment the foreshortened B-chain polypeptide contains Lysine (Lys) at position B28 and Proline (Pro) at position B29. In another embodiment the foreshortened B-chain polypeptide contains Aspartic acid (Asp) at position B28 and either Nle or Orn at position B29. In yet another embodiment, the insulin analogue is a mammalian insulin analogue, such as an analogue of human insulin. In one particular set of embodiments, the B-chain polypeptide comprises an amino-acid sequence, prior to trypsin treatment, of SEQ ID NO: 4 and polypeptides having three or fewer additional amino-acid substitutions thereof. In another particular set of embodiments, after digestion and semi-synthesis with trypsin, the resulting polypeptides may comprise a sequence selected from the group consisting of SEQ ID NOS: 5-7. In yet another particular set of embodiments, designated single-chain insulin analogues, the B-chain polypeptide is part of a single extended polypeptide of length 51-86 that comprises an amino-acid sequence provided in SEQ ID NO: 9, and polypeptides having three or fewer additional amino-acid substitutions thereof.

In addition or in the alternative, the insulin analogue may contain a non-standard amino-acid substitution at position 24 of the B-chain. In one particular example, the non-standard amino acid at B24 is Cyclohexanylalanine (Cha). In another particular example, the non-standard amino acid at B24 contains a halogenated aromatic ring, such as penta-fluoro-Phe, 2-F-Phe, 2-Cl-Phe, 2-Br-Phe, 4-F-Phe, 4-Cl-Phe, or 4-Br-Phe where "2" designates the a single halogenic substitution at the ortho position of the aromatic ring of Phe and where "4" designates the para position of the aromatic ring of Phe. In addition or in the alternative, the insulin analogue may contain an amino-acid substitution at position A8 whereby the β-branched side chain in wild-type insulin (Thr$^{A8}$) is substituted by a non-β-branched polar or charged side chain, such as Arg, Gln, Glu, His, or Lys.

Also provided is a nucleic acid encoding an insulin analogue comprising a B-chain polypeptide that incorporates a non-standard amino acid at position B24 or B29 or both. In one example, the non-standard amino acid is encoded by a stop codon, such as the nucleic acid sequence TAG. An expression vector may comprise such a nucleic acid and a host cell may contain such an expression vector.

Also provided is a nucleic acid encoding an insulin analogue comprising an A-chain polypeptide that incorporates a lysine (Lys) or Arginine (Arg) substitution at position A3 and optionally, other substitutions such as those giving rise to a glutamate substitution at position B29 or an amino acid other than Thr at position A8. An expression vector may comprise such a nucleic acid and a host cell may contain such an expression vector.

The invention also provides a method of treating a patient. The method comprises administering a physiologically effective amount of an insulin analogue or a physiologically acceptable salt thereof to the patient, wherein the insulin analogue or a physiologically acceptable salt thereof contains a foreshortened B-chain polypeptide lacking residues B1-B3 in combination of one or more additional substitutions at sites B24, B28, B29, or A8 as described above. In one embodiment, the foreshortened B-chain in the insulin analogue administered to a patient contains Glu at position B29. In still another embodiment, the insulin analogue is a mammalian insulin analogue, such as an analogue of human insulin. In one particular set of embodiments, the B-chain polypeptide comprises an amino-acid sequence selected from the group consisting of SEQ ID NOS: 5-7 and polypeptides having three or fewer additional amino-acid substitutions thereof.

BRIEF DESCRIPTION OF THE SEVERAL VIEWS OF THE DRAWINGS

FIG. 1B is a structural model of proinsulin, consisting of an insulin-like moiety and a disordered connecting peptide (dashed line).

FIGS. 2A and 2B provide molecular models showing the potential conformational variability of the N-terminal arm of insulin B-chain. Residues B1-B6 are shown in crystallographic T-state protomers (FIG. 2A) and ensemble of NMR-derived solution structures (FIG. 2B). The arms are in each case shown as sticks against a space-filling model of one representative structure. Gray scale code is shown at upper right of FIG. 2A. Structures in FIG. 2A were obtained from PDB depositions 4INS, 1APH, 1BPH, 1CPH, 1DPH, 1G7A, 1TRZ, 1TYL, 1TYM and 1ZNI; structures in FIG. 2B were obtained from PDB depositions 1TYL and 1G7A.

In FIG. 2A, relative activities for the B isoform of the insulin receptor (IR-B) are determined by competitive binding assay in which receptor-bound $^{125}$I-labeled human insulin is displaced by increasing concentrations of human insulin (■) or its analogues: Orn$^{B29}$-insulin (▲) and des-[B1-B3]-Orn$^{B29}$-insulin (▼). In FIG. 2B, relative activities for the Type I IGF receptor (IGF-1R) are determined by competitive binding assay in which receptor-bound $^{125}$I-labeled IGF-I is displaced by increasing concentrations of human insulin (■) or its analogues: Orn$^{B29}$-insulin (▲) and des-[B1-B3]-Orn$^{B29}$-insulin (▼).

DETAILED DESCRIPTION OF THE INVENTION

Figure 1A:
FIG. 1A is a schematic representation of the sequence of human proinsulin (SEQ ID NO: 1) including the A- and B-chains and the connecting region shown with flanking dibasic cleavage sites (filled circles) and C-peptide (open circles).
Figure 1C:
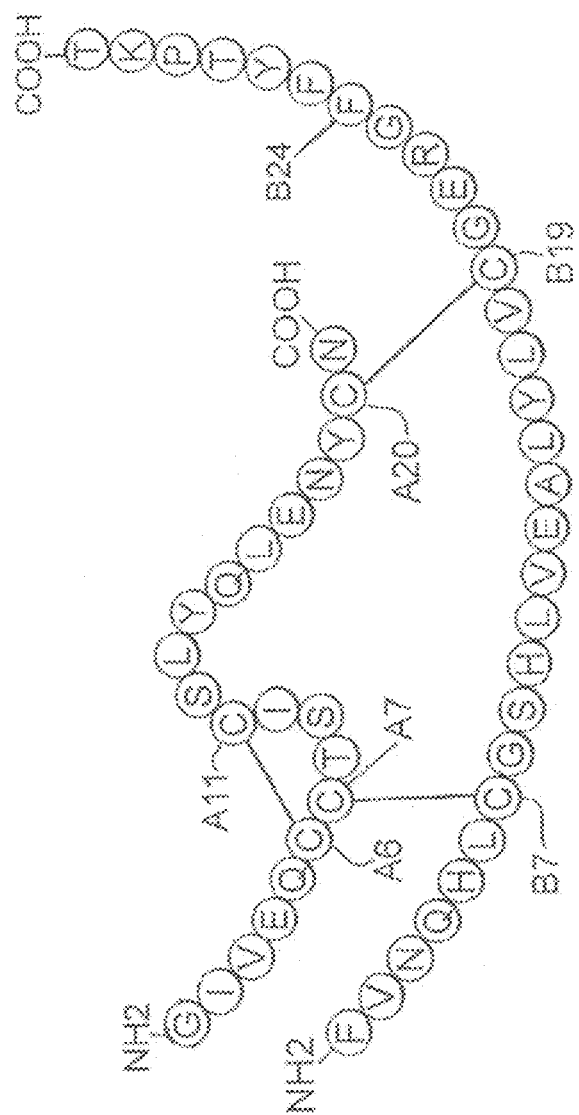
FIG. 1C is a schematic representation of the sequence of human insulin (SEQ ID NOS: 2 and 3) indicating the position of residue B24 in the B-chain.
Figure 2B:
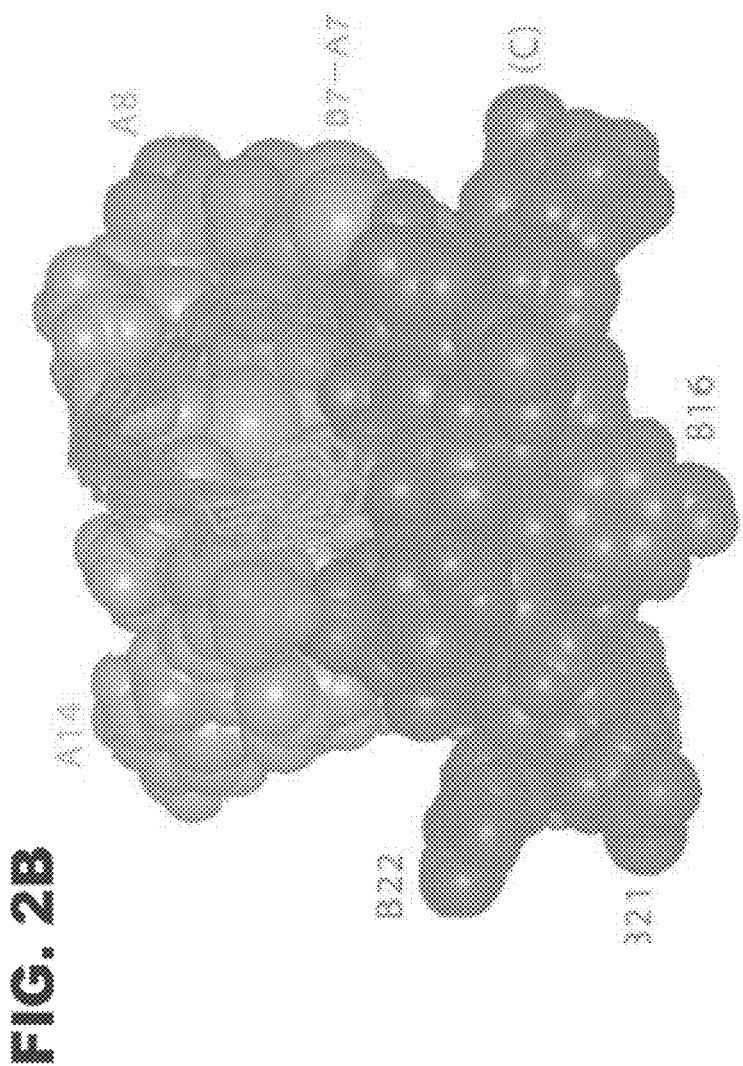

The present invention is directed toward an insulin analogue that provides resistance to fibrillation above room temperature where the analogue retains rapid hexamer disassembly and where the analogue then maintains at least a portion of biological activity of the corresponding unmodified insulin or insulin analogue.

The present invention pertains to removal of residues B1-B3 following the folding and disulfide pairing of a precursor molecule to improve the properties of the insulin analogue with respect to the lag time prior to onset of fibrillation. In one instance the removal of residues B1-B3 is combined with one or more amino-acid substitutions or modifications in the B23-B30 segment and in particular at positions B24, B28 and/or B29.

In one embodiment, the present invention provides an insulin analogue that provides more rapid hexamer disassembly by substitution of phenylalanine at position B24 by a non-standard amino acid, such as Cyclohexanylalanine (Cha) or a derivative of Phenylalanine containing a halogen atom (F, Cl, or Br) at the 4 position of the aromatic ring. In another particular embodiment the des-[B1-B3] analogue is enhanced with respect to thermodynamic stability by a substitution of $Phe^{B24}$ by a derivative containing a halogen atom (F, Cl, or Br) at the 2 position of the aromatic ring. In yet another embodiment the des-[B1-B3] analogue contains substitutions at positions B28 and/or B29 to confer more rapid rates of disassembly of the hexamer; examples known in the art are $Asp^{B28}$ (as in Novolog®), $Lys^{B28}$-$Pro^{B29}$ (as in Humalog®), and $Glu^{B29}$ (as in Apidra®). The present invention thus provides des-[B1-B3] forms of these analogues. The present invention is not limited, however, to human insulin and its analogues. It is also envisioned that these substitutions may also be made in animal insulins such as porcine, bovine, equine, and canine insulins, by way of non-limiting examples. In addition or in the alternative, the insulin analogue of the present invention may contain a non-standard amino-acid substitution at position 29 of the B chain, which is lysine (Lys) in wild-type insulin. In one particular example, the non-standard amino acid at B29 is ornithine (Orn); the non-standard amino acid at B29 could also be norleucine (Nle). Removal of residues B1-B3 may also be combined with an A-chain substitution by a non-beta-branched side chain at position A8, singly or in combination with the above modifications at positions B24, B28, or B29.

It has also been discovered that des-[B1-B3]-$Orn^{B29}$-insulin confers protection from fibrillation relative to wild-type insulin or $Orn^{B29}$-insulin without impairment of binding to the insulin receptor.

Furthermore, in view of the similarity between human and animal insulins, and use in the past of animal insulins in human patients with diabetes mellitus, it is also envisioned that other minor modifications in the sequence of insulin may be introduced, especially those substitutions considered "conservative." For example, additional substitutions of amino acids may be made within groups of amino acids with similar side chains, without departing from the present invention. These include the neutral hydrophobic amino acids: Alanine (Ala or A), Valine (Val or V), Leucine (Leu or L), Isoleucine (Ile or I), Proline (Pro or P), Tryptophan (Trp or W), Phenylalanine (Phe or F) and Methionine (Met or M). Likewise, the neutral polar amino acids may be substituted for each other within their group of Glycine (Gly or G), Serine (Ser or S), Threonine (Thr or T), Tyrosine (Tyr or Y), Cysteine (Cys or C), Glutamine (Glu or Q), and Asparagine (Asn or N). Basic amino acids are considered to include Lysine (Lys or K), Arginine (Arg or R) and Histidine (His or H). Acidic amino acids are Aspartic acid (Asp or D) and Glutamic acid (Glu or E). Unless noted otherwise or wherever obvious from the context, the amino acids noted herein should be considered to be L-amino acids. Standard amino acids may also be substituted by non-standard amino acids belong to the same chemical class. By way of non-limiting example, the basic side chain Lys may be replaced by basic amino acids of shorter side-chain length (Ornithine, Diaminobutyric acid, or Diaminopropionic acid). Lys may also be replaced by the neutral aliphatic isostere Norleucine (Nle), which may in turn be substituted by analogues containing shorter aliphatic side chains (Aminobutyric acid or Aminopropionic acid).

In one example, the insulin analogue of the present invention contains three or fewer conservative substitutions other than the removal of residues B1-B3 of the present invention.

As used in this specification and the claims, various amino acids in insulin or an insulin analogue may be noted by the amino-acid residue in question, followed by the position of the amino acid, optionally in superscript. The position of the amino acid in question includes the A- or B chain of insulin where the substitution is located. Thus, $Phe^{B1}$ denotes a phenylalanine as the first amino acid of the B chain of wild-type insulin; $Val^{B2}$ the second amino acid of the B-chain of wild-type insulin; and so forth until $Thr^{B30}$ at the C-terminal position. On removal of residues B1-B3 (designated as des-[B1-B3]), this numbering is retained such that $Glu^{B4}$ would be the first amino acid of the des-[B1-B3] B-chain, $Phe^{B24}$ is the 21$^{st}$ amino acid of the des-[B1-B3] B-chain, and so forth.

Although not wishing to be constrained by theory, the present invention envisions that residues B1-B3 defines a nonpolar arm that engages in non-native intermolecular interactions in the mechanism of formation of an amyloidogenic nucleus, and so its removal delays or prevents on the onset of fibrillation above room temperature. Substitution of the wild-type B3 residue (Gln) by a basic side chain (Lys or Arg) confers a novel tryptic site in the B-chain of a precursor insulin analogue or in the B-domain of a precursor single-chain polypeptide. Because this invention specifies the tryptic removal of residues B1-B3 occurs only after folding and native disulfide pairing of a precursor polypeptide have been accomplished, the critical role of residues B1-B3 in these processes is retained. Further, because this arm is not required for receptor binding or biological activity, it may be removed from the mature analogue product intended as a treatment of diabetes mellitus by subcutaneous injection or by continuous infusion via an external or internal pump.

We have found that the B1-B3 segment may readily be removed from insulin glulisine ([$Lys^{B3}$, $Glu^{B29}$]-insulin; the active component of Apidra®) by trypsin digestion to yield des-[B1-B3]-des-B23-B30]-insulin. The latter species was found to provide a starting material for the semi-synthesis of des-[B1-B3]-$Orn^{B29}$-insulin by trypsin-mediated semi-synthesis in the presence of an excess of the octapeptide GFFYTPOT (SEQ ID NO:10) where O designates Ornithine (Orn). It is also envisioned that the N-terminal B-chain deletion of the present invention may be made in any of a number of existing insulin analogues. For example, the B1-B3 segment may be removed from insulin lispro ([$Lys^{B28}$, $Pro^{B29}$]-insulin, herein abbreviated KP-insulin), insulin aspart ($Asp^{B28}$-insulin) via analogues of these products or corresponding single-chain precursors containing Lys or Arg at B3. These analogues are described in U.S. Pat. Nos. 5,149,777 and 5,474,978. These analogues are each known as fast-acting insulins.

The amino-acid sequence of human proinsulin is provided, for comparative purposes, as SEQ ID NO: 1.

(human proinsulin)
SEQ ID NO: 1
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Pro-Lys-Thr-Arg-Arg-Glu-Ala-Glu-Asp- Leu-Gln-Val-Gly-Gln-Val-Glu-Leu-Gly-Gly-Gly-Pro- Gly-Ala-Gly-Ser-Leu-Gln-Pro-Leu-Ala-Leu-Glu-Gly- Ser-Leu-Gln-Lys-Arg-Gly-Ile-Val-Glu-Gln-Cys-Cys- Thr-Ser-Ile-Cys-Ser-Leu-Tyr-Gln-Leu-Glu-Asn-Tyr- Cys-Asn The amino-acid sequence of the A chain of human insulin is provided as SEQ ID NO: 2.

(human A chain)
SEQ ID NO: 2
Gly-Ile-Val-Glu-Gln-Cys-Cys-Thr-Ser-Ile-Cys-Ser-

Leu-Tyr-Gln-Leu-Glu-Asn-Tyr-Cys-Asn

The amino-acid sequence of the B chain of human insulin is provided as SEQ ID NO: 3.

(human B chain)
SEQ ID NO: 3
Phe-Val-Asn-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Pro-Lys-Thr

The amino-acid sequence of a precursor B chain of human insulin may be modified with a substitution of a Lysine (Lys) or Arginine (Arg) at position B3 and optionally Glutamate (Glu) at position B29. An example of such a sequence is provided as SEQ ID NO: 4.

SEQ ID NO: 4
Phe-Val-Xaa$_1$-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Pro-Xaa$_2$-Thr
[Xaa$_1$ is Arg or Lys; Xaa$_2$ is Lys or Glu]

Following folding and trypsin digestion of a precursor analogue or precursor single-chain insulin analog containing Arg or Lys at position B3 and following trypsin mediated semi-synthesis with a modified octapeptide, the resulting des-(B1-B3) modification may optionally be combined with non-standard substitutions at other positions such as B24 as provided in SEQ ID NOS: 5-7.

SEQ ID NO: 5
Gln-His-Leu-Cys-Gly-Ser-Xaa$_3$-Leu-Val-Glu-Ala-Leu-

Tyr-Leu-Val-Cys-Gly-Glu-Arg-Gly-Xaa$_1$-Phe-Tyr-Thr-

Pro-Xaa$_2$-Thr
[Xaa$_1$ is Phe, Cha, penta-fluoro-Phe, 2F-Phe,
2-Cl-Phe, 2-Br-Phe, 4F-Phe, 4-Cl-Phe, or
4-Br-Phe; Xaa$_2$ is Glu, Lys, Ornithine,
Diaminobutyric acid, Diaminoproprionic acid,
Norleucine, Aminobutric acid, or Aminoproprionic
acid; Xaa$_3$ is His, Asp, Pro, or Glu]

SEQ ID NO: 6
Gln-His-Leu-Cys-Gly-Ser-Xaa$_3$-Leu-Val-Glu-Ala-Leu-

Tyr-Leu-Val-Cys-Gly-Glu-Arg-Gly-Xaa$_1$-Phe-Try-Thr-

Xaa$_2$-Pro-Thr
[Xaa$_1$ is Phe, Cha, penta-fluoro-Phe, 2F-Phe,
2-Cl-Phe, 2-Br-Phe, 4F-Phe, 4-Cl-Phe, or
4-Br-Phe; Xaa$_2$ is Lys, Arg, Ala, Glu, Gln, or Val;
Xaa$_3$ is His, Asp, Pro, or Glu]

SEQ ID NO: 7
Gln-His-Leu-Cys-Gly-Ser-Xaa$_2$-Leu-Val-Glu-Ala-Leu-

Tyr-Leu-Val-Cys-Gly-Glu-Arg-Gly-Xaa$_1$-Phe-Try-Thr-

Pro-Glu-Thr
[Xaa$_1$ is Phe, Cha, penta-fluoro-Phe, 2F-Phe,
2-Cl-Phe, 2-Br-Phe, 4F-Phe, 4-Cl-Phe, or
4-Br-Phe; Xaa$_2$ is His, Asp, Pro, or Glu]

The variant B-chains specified in SEQ ID 5-7 may be combined with an A-chain optionally containing substitutions at position A8 as given in SEQ ID NO: 8.

(human A chain)
SEQ ID NO: 8
Gly-Ile-Val-Glu-Gln-Cys-Cys-Xaa$_4$-Ser-Ile-Cys-Ser- Leu-Tyr-Gln-Leu-Glu-Asn-Tyr-Cys-Asn
[where Xaa$_4$ is Arg, Gln, Glu, His, Lys, or Thr]

Deletion of residues B1-B3 may also be effected in the context of analogues of human insulin containing His substitutions at residues A4, A8 and/or B1 as described more fully in co-pending International Application No. PCT/US07/00320 and U.S. application Ser. No. 12/160,187, the disclosures of which are incorporated by reference herein. For example, the trypsin-sensitive substitution of Arg or Lys at position B3 may be present with His$^{A8}$ and/or His$^{B1}$ substitutions in a single-chain insulin analogue or proinsulin analogue having the amino-acid sequence represented by SEQ ID NO: 9, SEQ ID NO: 9
Phe-Val-Xaa$_1$-Gln-His-Leu-Cys-Gly-Ser-His-Leu-Val- Glu-Ala-Leu-Tyr-Leu-Val-Cys-Gly-Glu-Arg-Gly-Xaa$_2$-

Phe-Tyr-Thr-Xaa$_3$-Xaa$_4$-Thr-Xaa$_5$-Gly-Ile-Val-Xaa$_6$-

Gln-Cys-Cys-Xaa$_7$-Ser-Ile-Cys-Ser-Leu-Tyr-Gln-Leu-

Glu-Asn-Tyr-Cys-Asn;

wherein Xaa$_1$ is Arg or Lys; wherein Xaa$_2$ is Phe, Cha, penta-fluoro-Phe, 2F-Phe, 2-Cl-Phe, 2-Br-Phe, 4F-Phe, 4-Cl-Phe, or 4-Br-Phe; wherein Xaa$_3$ is Pro, Lys, or Asp; wherein Xaa$_4$ is Lys or Pro; wherein Xaa$_6$ is His or Glu; wherein Xaa$_7$ is His, Lys, Arg, Glu, Gln or Thr; wherein Xaa$_5$ is 0-34 of any amino acid or a break in the amino-acid chain such that the C-terminal residue is Thr; and wherein Xaa$_6$ is Glu, His, Arg or Lys.

Trypsin-mediated semisynthesis employs synthetic octapeptides of SEQ ID NO: 10-15, which contain key receptor-binding determinants of intact insulin and share the property of not containing tryptic digestion sites.

```
                                              SEQ ID NO: 10
Gly-Phe-Phe-Tyr-Thr-Pro-Orn-Thr
[wherein Orn designates Ornithine]

SEQ ID NO: 11
Gly-Phe-Phe-Tyr-Thr-Pro-Glu-Thr

SEQ ID NO: 12
Gly-Phe-Phe-Tyr-Thr-Lys-Pro-Thr

SEQ ID NO: 13
Gly-Xaa₁-Phe-Tyr-Thr-Lys-Pro-Thr
[Wherein Xaa₁ is Cha, penta-fluoro-Phe, 2F-Phe,
2-Cl-Phe, 2-Br-Phe, 4F-Phe, 4-Cl-Phe, or 4-Br-
Phe]

SEQ ID NO: 14
Gly-Xaa₁-Phe-Tyr-Thr-Pro-Orn-Thr
[Wherein Xaa₁ is Cha, penta-fluoro-Phe, 2F-Phe,
2-Cl-Phe, 2-Br-Phe, 4F-Phe, 4-Cl-Phe, or 4-Br-
Phe]

SEQ ID NO: 15
Gly-Xaa₁-Phe-Tyr-Thr-Pro-Glu-Thr
[Wherein Xaa₁ is Cha, penta-fluoro-Phe, 2F-Phe,
2-Cl-Phe, 2-Br-Phe, 4F-Phe, 4-Cl-Phe, or 4-Br-
Phe]

SEQ ID NO: 16
Gly-Xaa₁-Phe-Tyr-Thr-Asp-Xaa₂-Thr
[Wherein Xaa₁ is Cha, penta-fluoro-Phe, 2F-Phe,
2-Cl-Phe, 2-Br-Phe, 4F-Phe, 4-Cl-Phe, or
4-Br-Phe; and wherein Xaa₂ is Ornithine,
Diaminobutyric acid, Diaminoproprionic acid,
Norleucine, Aminobutric acid, or Aminoproprionic
acid]
```

Analogues of insulin lacking residues B1-B3 were prepared using insulin glulisine (SEQ ID NO:2 and SEQ ID NO:4, Lys$^{B3}$, Glu$^{B29}$) as starting material. Complete trypsin digestion of this analogue yielded des-[B1-B3]-des-B23-B30]-insulin, which was purified by reverse-phase high-performance liquid chromatography (HPLC). From this fragment, which contains the three native disulfide bridges of wild-type insulin, modified B23-B30 peptide segments were attached by trypsin-catalyzed semi-synthesis and purified by high-performance liquid chromatography (Mirmira, R. G., and Tager, H. S., 1989. *J. Biol. Chem.* 264: 6349-6354.) This protocol employs (i) a synthetic octapeptide representing residues (N)-GFFYTPOT or (N)-GFFYTPET (substitutions underlined; SEQ ID NOS: 10 and 11, respectively) and (ii) truncated analogue des-tripeptide[B1-B3]-des-octapeptide[B23-B30]-insulin or, in the case of Glu$^{A8}$-insulin analogues, Glu$^{A8}$-des-tripeptide[B1-B3]-des-octapeptide[B23-B30]-insulin. Trypsin does not cleave after Orn. In brief, des-octapeptide (15 mg) and octapeptide (15 mg) were dissolved in a mixture of dimethylacetamide/1,4-butandiol/0.2 M Tris acetate (pH 8) containing 10 mM calcium acetate and 1 mM ethylene diamine tetra-acetic acid (EDTA) (35:35:30, v/v, 0.4 mL). The final pH was adjusted to 7.0 with 10 μL of N-methylmorpholine. The solution was cooled to 12° C., and 1.5 mg of TPCK-trypsin was added and incubated for 2 days at 12° C. An additional 1.5 mg of trypsin was added after 24 hr. The reaction was acidified with 0.1% trifluoroacetic acid and purified by preparative reverse-phase HPLC (C4). Mass spectrometry using matrix-assisted laser desorption/ionization time-of-flight (MALDI-TOF; Applied Biosystems, Foster City, Calif.) in each case gave expected values (not shown). The general protocol for solid-phase synthesis is as described (Merrifield et al., 1982. *Biochemistry* 21: 5020-5031). 9-fluoren-9-yl-methoxy-carbonyl (F-moc)-protected phenylalanine analogues were purchased from Chem-Impex International (Wood Dale, Ill.).

The above protocol was also employed to prepare des-tripeptide[B1-B3] analogues of human insulin containing Ornithine or Glutamic acid at position B29. The method of preparation of these analogues exploits non-standard amino-acid substitutions at position 29 to eliminate the tryptic site ordinarily present within the C-terminal octapeptide of the B chain (i.e., between Lys$^{B29}$ and Thr$^{B30}$) while maintaining a Proline at position 28. Pro$^{B28}$ contributes to the stability of the dimer interface within the insulin hexamer, and so this method of preparation provides near-isosteric models of wild-type insulin in which other modifications may conveniently be incorporated without the need for cumbersome side-chain protection.

Circular dichroism (CD) spectra were obtained at 4° C. and/or 25° C. using an Aviv spectropolarimeter (Weiss et al., *Biochemistry* 39: 15429-15440). Samples contained ca. 25 μM DKP-insulin or analogues in 50 mM potassium phosphate (pH 7.4); samples were diluted to 5 μM for guanidine-induced denaturation studies at 25° C. To extract free energies of unfolding, denaturation transitions were fitted by non-linear least squares to a two-state model as described by Sosnick et al., *Methods Enzymol.* 317: 393-409. In brief, CD data μ(x), where x indicates the concentration of denaturant, were fitted by a nonlinear least-squares program according to $$\theta(x) = \frac{\theta_A + \theta_B e^{\left(-\Delta G^0_{H_2O} - mx\right)/RT}}{1 + e^{-\left(\Delta G^0_{H_2O} - mx\right)/RT}}$$

where x is the concentration of guanidine and where $\theta_A$ and $v_B$ are baseline values in the native and unfolded states. Baselines were approximated by pre- and post-transition lines $\theta_A(x) = \theta_A^{H_2O} + m_A x$ and $\theta_B(x) = \theta_B^{H_2O} + m_B x$. The m values obtained in fitting the variant unfolding transitions are lower than the m value obtained in fitting the wild-type unfolding curve. To test whether this difference and apparent change in $\Delta G_u$ result from an inability to measure the CD signal from the fully unfolded state, simulations were performed in which the data were extrapolated to plateau CD values at higher concentrations of guanidine; essentially identical estimates of $\Delta G_u$ and m were obtained.

Figure 3:
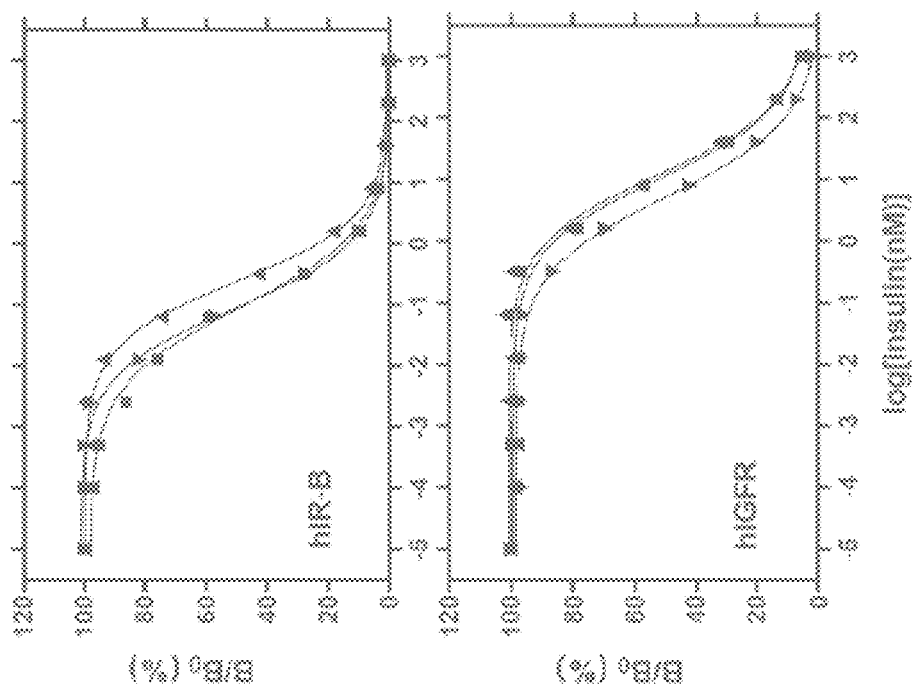
FIG. 3 is a pair of graphs showing the results of receptor-binding studies of insulin analogues.

Relative activity is defined as the ratio of the hormone-receptor dissociation constants of analogue to wild-type human insulin, as measured by a competitive displacement assay using $^{125}$I-human insulin. Microtiter strip plates (Nunc Maxisorb) were incubated overnight at 4° C. with AU5 IgG (100 μl/well of 40 mg/ml in phosphate-buffered saline). Binding data were analyzed by a two-site sequential model. Data were corrected for nonspecific binding (amount of radioactivity remaining membrane associated in the presence of 1 μM human insulin. In all assays the percentage of tracer bound in the absence of competing ligand was less than 15% to avoid ligand-depletion artifacts. Representative data are provided in FIG. 3A; corresponding assays conducted with the Type I IGF receptor (IGF-1R) are shown in FIG. 3B.

The far-ultraviolet circular dichroism (CD) spectrum of the des-tripeptide[B1-B3] analogue are similar to those of the parent analogues. Free energies of unfolding ($\Delta G_u$) at 25° C. were estimated based on a two-state model as extrapolated to zero denaturant concentration. Lag time indicates time (in days) required for initiation of protein fibrillation on gentle agitation at 30° C. in zinc-free phosphate-buffered saline (pH 7.4).

The baseline thermodynamic stability of wild-type insulin and Orn$^{B29}$-insulin, as inferred from a two-state model of denaturation at 25° C., are indistinguishable: 3.5±0.1 kcal/mole and 3.5±0.1 kcal/mole, respectively. CD-detected guanidine denaturation studies indicate that deletion of residues B1-B3 is associated with a small decrement in thermodynamic stability in the context of Orn$^{B29}$-insulin: $\Delta G_u$ 3.2±0.1 kcal/mole, implying that $\Delta\Delta G_u$ 0.3±0.2 kcal/mole. Nonetheless, the physical stability of the des-[B1-B3] analogue was found to be greater than that of wild-type insulin or Orn$^{B29}$-insulin as evaluated in triplicate during incubation in 300 µM phosphate-buffered saline (PBS) at pH 7.4 at 30° C. under gentle agitation. The samples were observed for 10 days or until signs of precipitation or frosting of the glass vial were observed. Whereas the three tubes of wild-type insulin and three tubes of Orn$^{B29}$-insulin became cloudy in less than 4 days, the three tubes of des-[B1-B3]-Orn$^{B29}$-insulin stayed clear for at least 7 days. Similar comparison of fibrillation lag times between des-[B1-B3]-Glu$^{B29}$-insulin and [Lys$^{B3}$, Glu$^{B29}$]-insulin (the active component of Apidra®) showed that removal of residues B1-B3 lengthened the lag time by at least a factor of two.

Dissociation constants ($K_d$) were determined as described by Whittaker and Whittaker (2005. *J. Biol. Chem.* 280: 20932-20936), by a competitive displacement assay using $^{125}$I-Tyr$^{414}$-insulin (kindly provided by Novo-Nordisk) and the purified and solubilized insulin receptor (isoform B or A) in a microtiter plate antibody capture assay with minor modification; transfected receptors were tagged at their C-terminus by a triple repeat of the FLAG epitope (DYKDDDDK) and microtiter plates were coated by anti-FLAG M2 monoclonal antibody (Sigma). The percentage of tracer bound in the absence of competing ligand was less than 15% to avoid ligand-depletion artifacts. Binding data were analyzed by non-linear regression using a heterologous competition model (Wang, 1995, *FEBS Lett.* 360: 111-114) to obtain dissociation constants. Results are provided in Table 1; dissociation constants are provided in units of nanomolar. Interestingly, removal of residues B1-B3 appears to enhance receptor binding by at least twofold.

TABLE 1

Binding of Insulin Analogues to
Insulin Receptor and IGF Receptor

| Protein | IR-B binding | IGF-1R binding |
|---|---|---|
| insulin | 0.061 ± 0.010 nM | 6.4 ± 1.0 nM |
| Orn$^{B29}$-insulin | 0.118 ± 0.018 nM | 7.5 ± 1.2 nM |
| des-[B-B3]-Orn$^{B29}$-insulin | 0.035 ± 0.006 nM | 3.2 ± 0.5 nM |

IR-B, B isoform of the insulin receptor; IGF-1R, Type 1 IGF receptor

Figure 4:
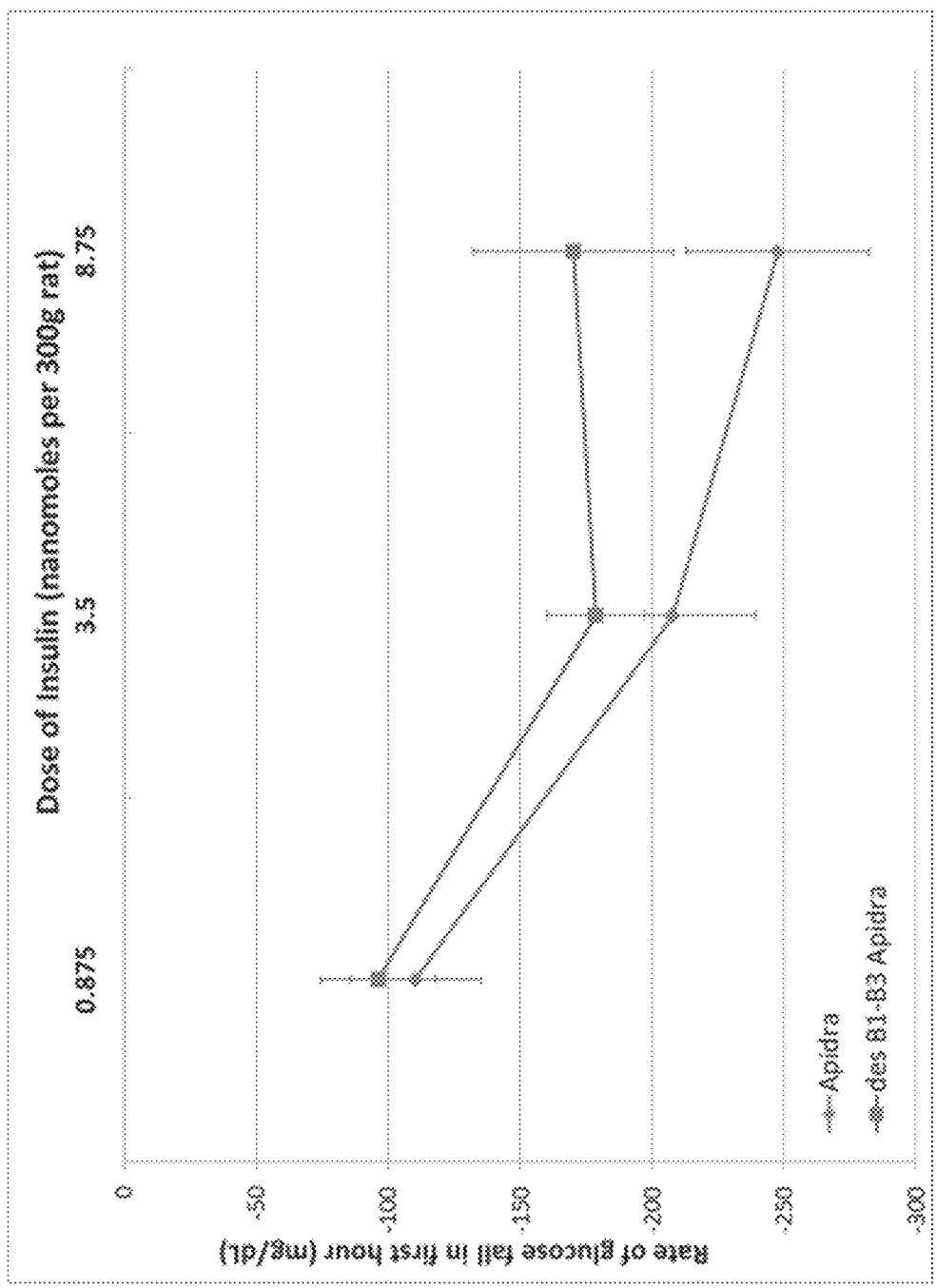
FIG. 4 is a graph showing the dose-response of des-[B1-B3] Apidra® insulin (Glu$^{B29}$; ■) versus full length Apidra® insulin (Lys$^{B3}$, Glu$^{B29}$) (♦). The graph shows the rate of decrease of blood sugar levels in the first hour after administration versus the dose of insulin in nanomoles per 300 g rat.

Referring to FIG. 4, Glulisine-insulin (Apidra®, SEQ ID NOS:2 and 4, ♦) and des-[B1-3] glulisine insulin (SEQ ID NOS:2 and 5; ■) were purified by HPLC, lyophilized to powder, and dissolved in insulin diluent. Male Lewis rats were injected subcutaneously at time=0 with either 0.875, 3.5 or 8.75 mM of glulisine or des-[B1-3 glulisine in 100 µl of diluent; the higher dose is at the plateau of the wild-type insulin dose-response curve whereas the lower dose corresponds to about 40% maximal initial rate of glucose disposal. Injection of diluent alone was performed as a negative control. 6 rats were studied in each group. Blood was obtained from clipped tip of the tail at time 0 and at successive intervals up to 120 min. Blood glucose was measured using a Hypoguard Advance Micro-Draw meter. Blood glucose concentrations were observed to decrease. Any differences in initial rate or duration were not statistically significant.

A method for treating a patient comprises administering an insulin analogue containing a foreshortened des-tripeptide[B1-B3] B-chain as known in the art or described herein. It is another aspect of the present invention that des-tripeptide[B1-B3]-des-octapeptide [B23-B30]-insulin may readily be obtained by tryptic digestion of a two-chain or single-chain precursor polypeptide following its folding to achieve native disulfide pairing. It is yet another aspect of the present invention that use of non-standard amino-acid substitutions enables a rapid and efficient method of preparation of insulin analogues by trypsin-mediated semi-synthesis using unprotected octapeptides.

In still another example, the insulin analogue is administered by an external or implantable insulin pump. An insulin analogue of the present invention may also contain other modifications, such as a tether between the C-terminus of the B-chain and the N-terminus of the A-chain as described more fully in co-pending U.S. patent application Ser. No. 12/419,169, the disclosure of which is incorporated by reference herein.

A pharmaceutical composition may comprise such insulin analogues and which may optionally include zinc. Zinc ions may be included in such a composition at a level of a molar ratio of between 2.2 and 3.0 per hexamer of the insulin analogue. In such a formulation, the concentration of the insulin analogue would typically be between about 0.1 and about 3 mM; concentrations up to 3 mM may be used in the reservoir of an insulin pump. Modifications of meal-time insulin analogues may be formulated as described for (a) "regular" formulations of Humulin® (Eli Lilly and Co.), Humalog® (Eli Lilly and Co.), Novalin® (Novo-Nordisk), and Novalog® (Novo-Nordisk) and other rapid-acting insulin formulations currently approved for human use, (b) "NPH" formulations of the above and other insulin analogues, and (c) mixtures of such formulations. Analogues of insulin lacking residues B1-B3 and containing Glu$^{B29}$ may also be formulated in the absence of zinc ions as known in the art for the formulation of insulin glulisine.

Excipients may include glycerol, glycine, arginine, Tris, other buffers and salts, and anti-microbial preservatives such as phenol and meta-cresol; the latter preservatives are known to enhance the stability of the insulin hexamer. Such a pharmaceutical composition may be used to treat a patient having diabetes mellitus or other medical condition by administering a physiologically effective amount of the composition to the patient.

A nucleic acid comprising a sequence that encodes a polypeptide encoding an insulin analogue containing a sequence encoding at least a B-chain of insulin with Arg or Lys at position B3 with a non-standard amino acid at position B24 is also envisioned. The latter can be accomplished through the introduction of a stop codon (such as the amber codon, TAG) at position B24 in conjunction with a suppressor tRNA (an amber suppressor when an amber codon is used) and a corresponding tRNA synthetase, which incorporates a non-standard amino acid into a polypeptide in response to the stop codon, as previously described (Furter, 1998, *Protein Sci.* 7:419-426; Xie et al., 2005, *Methods.* 36: 227-238). The particular sequence may depend on the preferred codon usage of a species in which the nucleic-acid sequence will be introduced. The nucleic acid may also encode other modifications of wild-type insulin. The nucleic-acid sequence may encode a modified A- or B-chain sequence containing an unrelated substitution or extension elsewhere in the polypeptide or modified proinsulin analogues. The nucleic acid may also be a portion of an expression vector, and that vector may be inserted into a host cell such as a prokaryotic host cell like an E. coli cell line, or a eukaryotic cell line such as S. cereviciae or Pischia pastoris strain or cell line.

For example, it is envisioned that synthetic genes may be synthesized to direct the expression of a B-chain polypeptide in yeast Piscia pastoris and other microorganisms. The nucleotide sequence of a B-chain polypeptide utilizing a stop codon at position B24 for the purpose of incorporating a Cyclohexanylalanine or halogen derivative of Phe at that position may be either of the following or variants thereof:

(a) with Human Codon Preferences:
(SEQ ID NO: 17)
TTTGTGXXXCAACACCTGTGCGGCTCACACCTGGTGGAAGCTCTCTACC TAGTGTGCGGGGAACGAGGCTAGTTCTACACACCCAAGACC
[wherein XXX is AGG, AGA, CGG or CGC (encoding Arg), or AAG or AAA (encoding Lys)]

(b) with Pichia Codon Preferences:
(SEQ ID NO: 18)
TTTGTTXXXCAACATTTGTGTGGTTCTCATTTGGTTGAAGCTTTGTACT TGGTTTGTGGTGAAAGAGGTTAGTTTTACACTCCAAAGACT
[wherein XXX is AGA, CGU or AGG (encoding Arg) or AAG or AAA (encoding Lys)]

Similarly, a full length proinsulin cDNA having human codon preferences, encoding Arg or Lys at position B3 and utilizing a stop codon at position B24 for the purpose of incorporating Cyclohexanylalanine or a halogenated derivative of Phe at that position may have the sequence of SEQ ID NO: 19.

(SEQ ID NO: 19)
TTTGTXXXCC AACACCTGTG CGGCTCACAC CTGGTGGAAG

CTCTCTACCT AGTGTGCGGG GAACGAGGCT AGTTCTACAC

ACCCAAGACC CGCCGGGAGG CAGAGGACCT GCAGGTGGGG

CAGGTGGAGC TGGGCGGCGG CCCTGGTGCA GGCAGCCTGC

AGCCCTTGGC CCTGGAGGGG TCCCTGCAGA AGCGTGGCAT

TGTGGAACAA TGCTGTACCA GCATCTGCTC CCTCTACCAG

CTGGAGAACT ACTGCAACTA G
[wherein XXX is AGG, AGA, CGG or CGC (encoding Arg), or AAG or AAA (encoding Lys)]

Likewise, a full-length human proinsulin cDNA utilizing a stop codon at position B24 for the purpose of incorporating a Cyclohexanylalanine or halogenated derivative of Phe at that position and having codons preferred by P. pastoris may have the sequence of SEQ ID NO: 20.

(SEQ ID NO: 20)
TTTGTTXXXC AACATTTGTG TGGTTCTCAT TTGGTTGAAG

CTTTGTACTT GGTTTGTGGT GAAAGAGGTT AGTTTTACAC

TCCAAAGACT AGAAGAGAAG CTGAAGATTT GCAAGTTGGT

CAAGTTGAAT TGGGTGGTGG TCCAGGTGCT GGTTCTTTGC

AACCATTGGC TTTGGAAGGT TCTTTGCAAA AGAGAGGTAT

TGTTGAACAA TGTTGTACTT CTATTTGTTC TTTGTACCAA

TTGGAAAACT ACTGTAACTA A
[wherein XXX is AGA, CGU or AGG (encoding Arg) or AAG or AAA (encoding Lys)]

Other variants of these sequences, encoding the same polypeptide sequence, are possible, given the synonyms in the genetic code.

Based upon the foregoing disclosure, it should now be apparent that insulin analogues provided will carry out the objects set forth hereinabove. Namely, these insulin analogues exhibit enhanced resistance to fibrillation while retaining rapid action due to hexamer disassembly and maintaining at least a fraction of the biological activity of wild-type insulin. It is, therefore, to be understood that any variations evident fall within the scope of the claimed invention and thus, the selection of specific component elements can be determined without departing from the spirit of the invention herein disclosed and described.

The following literature is cited to demonstrate that the testing and assay methods described herein would be understood by one of ordinary skill in the art.

Furter, R., 1998. Expansion of the genetic code: Site-directed p-fluoro-phenylalanine incorporation in *Escherichia coli*. Protein Sci. 7:419-426.

Merrifield, R. B., Vizioli, L. D., and Boman, H. G. 1982. Synthesis of the antibacterial peptide cecropin A (1-33). Biochemistry 21: 5020-5031.

Mirmira, R. G., and Tager, H. S. 1989. Role of the phenylalanine B24 side chain in directing insulin interaction with its receptor: Importance of main chain conformation. J. Biol. Chem. 264: 6349-6354.

Sosnick, T. R., Fang, X., and Shelton, V. M. 2000. Application of circular dichroism to study RNA folding transitions. Methods Enzymol. 317: 393-409.

Wang, Z. X. 1995. An exact mathematical expression for describing competitive biding of two different ligands to a protein molecule FEBS Lett. 360: 111-114.

Weiss, M. A., Hua, Q. X., Jia, W., Chu, Y. C., Wang, R. Y., and Katsoyannis, P. G. 2000. Hierarchiacal protein "un-design": insulin's intrachain disulfide bridge tethers a recognition α-helix. Biochemistry 39: 15429-15440.

Whittaker, J., and Whittaker, L. 2005. Characterization of the functional insulin binding epitopes of the full length insulin receptor. J. Biol. Chem. 280: 20932-20936.

Xie, J. and Schultz, P. G. 2005. An expanding genetic code. Methods. 36: 227-238.

What is claimed is:

1. A method for preparing a des-tripeptide [B1-B3] insulin analogue, the method comprising:
    providing a folded single-chain or two-chain insulin-related precursor polypeptide containing Arg or Lys at position B3;
    adding trypsin to the folded single-chain or two-chain insulin-related precursor polypeptide under conditions conducive to the proteolytic activity of trypsin to provide a reaction mixture;
    incubating the reaction mixture for sufficient time to yield a des-tripeptide[B1-B3]-des-octapeptide [B23-B30]-insulin intermediate product;
    adding a synthetic peptide in molar excess, wherein the synthetic peptide comprises residues corresponding to residues B23-B30 of insulin or an analogue thereof;
    adding trypsin under conditions conducive to the enzymatic activity of trypsin such that trypsin catalyzes formation of a peptide bond between ArgB22 of the des-tripeptide [B1-B3]-des-octapeptide [B23-B30]-insulin intermediate product and the synthetic peptide to yield the des-[B1-B3]insulin analogue.

2. The method of claim 1, wherein the folded single-chain or two-chain insulin-related precursor polypeptide is prepared by recombinant expression in a host cell.

3. The method of claim 2, wherein the des-[B1-B3]insulin analogue has the amino acid sequence of SEQ ID NO: 5, 6, or 7.

4. The method of claim 1, wherein the B23-B30 peptide segment has an amino acid sequence selected from SEQ ID NOS: 10-16.

5. The method of claim 1, wherein the des-[B1-B3]insulin analogue further comprises a B29 substitution.

6. The method of claim 5, wherein the substitution at B29 is selected from $Glu^{B29}$, $Orn^{B29}$, Diaminobutyric $acid^{B29}$, Diaminoproprionic $acid^{B29}$, $Norleucine^{B29}$, Aminobutric $acid^{B29}$, or Aminoprioprionic $acid^{B29}$.

7. The method of claim 1, wherein the des-[B1-B3]insulin analogue further comprises a substitution at B24.

8. The method of claim 7, wherein the substitution at B24 is selected from $Cha^{B24}$, penta-fluoro-$Phe^{B24}$, 2F-$Phe^{B24}$, 2-Cl-$Phe^{B24}$, 2-Br-$Phe^{B24}$, 4F-$Phe^{B24}$, 4-Cl-$Phe^{B24}$, or 4-Br-$Phe^{B24}$.

9. The method of claim 1, wherein the des-[B1-B3]insulin analogue further comprises a substitution at B10.

10. The method of claim 9, wherein the substitution at B10 is selected from a $Asp^{B10}$, $Pro^{B10}$, or $Glu^{B10}$ substitution.

* * * * *